US006017558A

United States Patent [19]

Bertholet

[11] Patent Number: 6,017,558

[45] Date of Patent: Jan. 25, 2000

[54] INCORPORATION OF A WATER-SOLUBLE ACTIVE PRINCIPLE IN A LIPID

[75] Inventor: Raymond Bertholet, Blonay, Switzerland

[73] Assignee: Nestec S.A., Vevey, Switzerland

[21] Appl. No.: 08/967,214

[22] Filed: Oct. 28, 1997

Related U.S. Application Data

[63] Continuation-in-part of application No. 08/491,006, Jun. 15, 1995, abandoned.

[30] Foreign Application Priority Data

Jun. 17, 1994 [EP] European Pat. Off. .............. 94109356

[51] Int. Cl.[7] .................................................... A61K 9/127

[52] U.S. Cl. ........................... 424/450; 424/401; 424/439

[58] Field of Search .................................... 424/450, 439, 424/401

[56] References Cited

U.S. PATENT DOCUMENTS

| | | | |
|---|---|---|---|
| 3,701,668 | 10/1972 | Morse | 99/91 |
| 4,999,208 | 3/1991 | Lengerich | 426/549 |
| 5,084,289 | 1/1992 | Shin | 426/330.6 |
| 5,284,941 | 2/1994 | Colarow | 536/127 |

FOREIGN PATENT DOCUMENTS

| | | |
|---|---|---|
| 0326829 | 1/1989 | European Pat. Off. . |
| 0365868 | 5/1990 | European Pat. Off. . |
| 0422543 | 4/1991 | European Pat. Off. . |
| 2627385 | 8/1989 | France . |
| 9015537 | 12/1990 | WIPO . |

OTHER PUBLICATIONS

Pharmacological and Chemical Synonyms, E. E. J. Marler, Ed., 6th ed., p. 361, 1976.

Textbook of Biochemistry with Clinical Correlations, T. M. Devlin, Ed., pp. 490–491, 1982.

Derwent Publications, database WPI, AN 88–087108& JP–A–63 036 792, Feb. 17, 1988 and Patent Abstracts of Japan, vol. 12, No. 248 (C–511), Jul. 13, 1988.

Derwent Publications, database WPI, AN 87–112992 and JP–A–62 059 287.

*Primary Examiner*—Thurman K. Page
*Assistant Examiner*—Todd Ware
*Attorney, Agent, or Firm*—Pennie & Edmonds

[57] ABSTRACT

To incorporate a water-soluble active principle in a stable lipidic phase, the water-soluble active principle is added with stirring in the presence of water to a fat containing a lecithin fraction low in phosphatidyl choline and the heterogeneous mixture obtained is dried to form a homogeneous micellar phase.

17 Claims, No Drawings

INCORPORATION OF A WATER-SOLUBLE ACTIVE PRINCIPLE IN A LIPID

This is a continuation-in-part of application Ser. No. 08/491,006, filed Jun. 15, 1995, now abandoned.

TECHNICAL FIELD

This invention relates to a process for incorporating a water-soluble active principle in a lipid and, more particularly, for stabilizing a water-soluble antioxidant in a lipidic phase.

BACKGROUND ART

The majority of oils and certain fats used in food, cosmetic and pharmaceutical products are rich in polyunsaturated fatty acids and, because of this, are particularly sensitive to oxidation. Their stability can be improved by the addition of synthetic antioxidants such as, for example, BHA (butyl hydroxyanisole), BHT (butyl hydroxytoluene) or TBHQ (tert.butyl hydroquinone). Unfortunately, the harmlessness of these compounds is questionable.

Attempts have been made to replace these synthetic antioxidants with natural antioxidant compounds of the fat-soluble type such as, for example, the tocopherols or ascorbyl palmitate or of the water-soluble type such as, for example, ascorbic acid, vegetable extracts, organic acids or amino acids. In the case of the water-soluble compounds, an emulsifier, such as a phospholipid for example, has to be used for incorporating the water-soluble antioxidants in the oils in the form of micelles.

By virtue of their structure, the phospholipids are capable of creating associations with certain water-soluble compounds to form micelles which, for their part, are fat-soluble.

The incorporation of vitamin C or other water-soluble compounds in oils using phospholipids is known, for example, from European patent application 0 326 829. Unfortunately, this known process uses an organic solvent, for example ethanol, which promotes the formation of a single phase in view of its hydrophilic and lipophilic properties. In addition, the process in question—which uses an unfractionated soya lecithin—is attended by the disadvantage that problems of color, odor and flocculation in storage cannot be avoided.

According to U.S. Pat. No. 5,084,289, inverse micelles, i.e. micelles in which the continuous phase is the lipophilic phase, are formed by dissolving in an oil a phospholipid and then a small quantity of an aqueous solution containing a water-soluble antioxidant, for example vitamin C, in a high concentration. The mixture is stirred to form inverse micelles, a single phase thus being obtained. The small quantity of aqueous phase relative to the lipidic phase makes homogenization difficult or even virtually impossible on a large scale. In addition, it is only possible by this process to incorporate substances highly soluble in water, for example vitamin C, and not sparingly water-soluble substances such as, for example, ethylene dinitrotetraacetic acid (EDTA). Finally, this process does not avoid the appearance of undesirable colors and odors in storage because the lecithin is not fractionated.

It has now surprisingly been found that these disadvantages can be completely eliminated by using a phospholipid fraction substantially free from phosphatidyl choline.

SUMMARY OF THE INVENTION

Accordingly, the present invention relates to a process for incorporating a water-soluble active principle in a fat in the presence of phospholipids, characterized in that the phospholipids are treated to produce a phospholipid fraction substantially free from phosphatidyl choline, an aqueous solution of the water-soluble active principle is incorporated in the mixture of this fraction and fat in liquid form with vigorous stirring in a quantity sufficient to hydrate the phospholipid fraction to form a heterogeneous mixture and the mixture obtained is dried and thus becomes homogeneous.

DETAILED DESCRIPTION OF THE INVENTION

In the context of the present invention, a "phospholipid fraction substantially free from phosphatidyl choline" is understood to be a fraction obtained from commercial phospholipids, for example soya, by a treatment which enables the phosphatidyl choline to be separated from the other constituents, such as phosphatidyl ethanolamine, phosphatidyl inositol and phosphatidic acid, hereinafter referred to as "other PLS" (other phospholipids).

In a first embodiment, the commercial phospholipid are treated in solution in the oil with an adsorbent, after which the oil thus treated is separated to form the phospholipid fraction.

The adsorbent is included in an amount which is greater than the amount of phospholipids to thus remove substantially all of the phosphatidyl choline from the lecithin and form the phospholipid fraction. The amount of adsorbent used is preferably about two to four times greater than the amount of phospholipids. The most advantageous adsorbent is a bleaching earth, with a commercially available product known as Tonsil Optimum FF being preferred.

In a second embodiment, which is preferred, the phospholipids is treated in solution in a mixture of organic solvents by liquid chromatography in a column of silica gel in known manner and the phospholipid fraction containing the other PLS, which is also freed from most of the triglycerides, is collected.

The amount of the phospholipid fraction included in these compositions is sufficient to combine with the water-soluble active ingredient and the water to form a homogeneous composition. These amounts will typically range from about 5 to 40% by weight of the water-containing composition, and from about 0.2 to 5% by weight of the final micellar phase.

The water-soluble active principles envisaged in accordance with the invention are, for example, cosmetic or dermatological agents or water-soluble antioxidants. They include, for example, conventional antioxidants, for example vitamin C, vegetable extracts, for example rosemary, green tea, organic acids, for example hydroxy acids, such as citric acid, phenolic acids, for example caffeic, quinic and chlorogenic acids, caffeine, amino acids, phenyl indanes and sequestering agents, for example citrates or EDTA. The amount of the active principle will typically range from about 1 to 10% by weight of the water-containing composition, and from about 0.02 to 1% by weight of the final micellar phase.

The fat to be protected against oxidation is rich in unsaturated fatty acids, more particularly polyunsaturated fatty acids. The fat may be a vegetable oil, for example sunflower oil, wheat germ oil, grapeseed oil, corn oil, safflower oil, olive oil, evening primrose oil, borage oil and blackcurrant seed oil, or an animal oil, for example chicken fat, butter oil, or a marine animal oil, more particularly fish oil. The amount of the water-containing composition will typically range from about 2 to 10% by weight of the fat.

The incorporation of the water-soluble active principle takes place with vigorous stirring at a temperature above 60° C. and preferably at a temperature on the order of 80° C. The water-soluble active principle may be introduced in the form of an aqueous solution or, alternatively, in dry form, in which case water is subsequently added. The quantity of water in the mixture should be sufficient to hydrate the quantity of phospholipid fraction which it contains. It represents typically 2 to 8% by weight of the mixture and, preferably, approximately 5% thereof. This operation takes place over a period of 10 to 30 minutes in the absence of air, for example in a nitrogen atmosphere, which results in the formation of a heterogeneous mixture.

The water is then eliminated from the heterogeneous mixture by heating in vacuo, preferably to 60 to 90° C. and advantageously to 60 to 70° C. under a vacuum of 0.5 to 35 mbar. A homogeneous and stable micellar phase is formed.

EXAMPLES

The invention is illustrated by the following Examples in which parts and percentages are by weight, unless otherwise indicated.

Example 1

A refined soya phospholipid mixture low in heavy metals (Top-cithin 200®) and containing 60% of phospholipids (referred to hereinafter as PLS) is dissolved under nitrogen in a sunflower oil (SFO).

The solution is then treated with a bleaching earth (Tonsil Optimum FF®) for 30 minutes at 85 to 90° C., under a pressure of 35 mbar and in the presence of a foam inhibitor (Rhodosil 70414®), the quantity of adsorbent corresponding to four times the quantity of phospholipids, after which the solution is separated from the adsorbent by filtration.

The quantities shown in Table 1 below of vitamin C and EDTA in solid form and then 5% of demineralized water are subsequently added to the solution. After vigorous stirring under nitrogen for 15 minutes at 80° C., a heterogeneous mixture is obtained and is then dried for 30 minutes at 80–90° C. under a pressure of 35 mbar and then 0.5 mbar and filtered. A homogeneous micellar phase is obtained.

The stabilized oil (1a) is evaluated by comparison with the same, unstabilized oil (1b) and with an oil stabilized with a commercial phospholipids which has not been treated with bleaching earth (1c):

From the point of view of their stability to oxidation as measured by the Rancimat® accelerated oxidation test at 110° C. The induction times obtained, expressed in h, represent the OSI (oil stability index) values.

From the point of view of their stability in storage at 15° C. by visual and olfactory assessment.

The results obtained are set out in Table 1 below:

TABLE 1

| Test | PL mg/kg | Vit. C mg/kg | EDTA mg/kg | Treatment | OSI, 110° C., h | Color |
|---|---|---|---|---|---|---|
| 1a | 10000 | 1000 | 200 | Yes | 19.5 | Yellow |
| 1b | — | — | — | — | 5 | Light yellow |
| 1c | 10000 | 1000 | 200 | No | 17.5 | Orange-yellow |

It can be seen that the treatment of phospholipids with a bleaching earth improves its color and increases its stability to oxidation.

Examples 2–10

SFO is stabilized in the same way as in Example 1 using vitamin C in conjunction with various sequestering agents in various quantities. The OSI values of unstabilized SFO (2a) and SFO containing the PL fraction treated with the adsorbent (2b) are measured by way of comparison.

The protection factor (PF), which corresponds to the quotient:

PF=OSI of the stabilized oil/OSI of the unstabilized oil (this quotient represents the increase in the induction time), is calculated from the OSI values.

The results are set out in Table 2 below:

TABLE 2

| Example | PL mg/kg | Vit. C mg/kg | Sequestrant, SA | SA mg/kg | OSI 110° C., h | PF | Stability at 15° C. after 5d |
|---|---|---|---|---|---|---|---|
| 2a | — | — | — | — | 5 | 1 | Clear |
| 2b | 5000 | — | — | — | 5.7 | 1.14 | Clear |
| 2 | 5000 | 1000 | — | — | 19 | 3.8 | Slightly cloudy |
| 3 | 5000 | 1000 | EDTA | 100 | 22.5 | 4.5 | Slightly cloudy |
| 4 | 5000 | 1000 | EDTA | 200 | 22 | 4.4 | Clear |
| 5 | 5000 | 1000 | EDTA | 400 | 20 | 4 | Clear |
| 6 | 5000 | 1000 | EDTA Na2 | 200 | 21 | 4.2 | Slightly cloudy |
| 7 | 5000 | 1000 | Citric acid | 200 | 17 | 3.4 | Slightly cloudy |
| 8 | 5000 | 1000 | Citric acid Na3 | 200 | 20.5 | 4.1 | Slightly cloudy |
| 9 | 5000 | 1000 | Citric acid Na3 | 400 | 16 | 3.2 | Clear |
| 10 | 5000 | 1000 | EDTA citric acid Na3 | 200 | 21.8 | 4.36 | Slightly cloudy |

It can be seen that the use of PL on its own is not sufficient to stabilize the oil (2b compared with 2a).

Examples 11–15

Following the procedure of Example 1, SFO stabilized with various ratios of vit.C to PL is evaluated for stability in storage, OSI and PF. The results are set out in Table 3 below by comparison with the unprotected oil (11a) and with the same oil to which 1.66% of a ternary mixture of vit.C, PL and vit.E in quantities of 1000 mg/kg vit.C, 4500 mg/kg PL and 500 mg/kg vit.E is added (11b).

TABLE 3

| Example | PL mg/kg | Vit. C mg/kg | EDTA mg/kg | Vit. C/PL × 100 | OSI 110° C., h | PF | Stability at 15° C. after 5d |
|---|---|---|---|---|---|---|---|
| 11a | — | — | — | — | 5 | 1 | Clear |
| 11b | 4500 | 1000 +500 mg/kg vit. E | — | 22 | 15.8 | 3.16 | Slightly cloudy |
| 11 | 2500 | 1000 | 200 | 40 | 14.7 | 2.94 | Slightly cloudy |
| 12 | 5000 | 1000 | 200 | 20 | 22 | 4.4 | Slightly cloudy |
| 13 | 6600 | 1000 | 200 | 15 | 20.8 | 4.16 | Slightly cloudy |
| 14 | 7500 | 1000 | 200 | 13.3 | 20 | 4 | Clear |
| 15 | 10000 | 1000 | 200 | 10 | 20 | 4 | Clear |

It can be seen that the use of a ternary mixture comprising vit.E does not improve the stability of the oil or its antioxidant properties in relation to the use of a mixture of PL and vit.C (11b compared with 11–15). Accordingly, it may be concluded that the synergism between vit.C and vit.E already occurs with the vit.E naturally present in SFO (corresponding to 760 mg/kg). Accordingly, for vegetable oils naturally containing vit.E, the addition of more vit.E is not beneficial.

The stabilized oils were stored for 1 month at 15° C. It was found that the oils stabilized with a ratio of vit.C to PL of greater than 13% became cloudy during that period. Accordingly, this ratio is preferably less than or equal to 13% to ensure optimal stability of the oil.

Examples 16–19

Following the procedure of Example 1, SFO stabilized with various quantities of vit.C (the ratio of vit.C to PL being constant) was evaluated for stability in storage, OSI and PF. The results obtained are set out in Table 4 below by comparison with the unprotected oil (16a).

TABLE 4

| Example | PL mg/kg | Vit. C mg/kg | EDTA mg/kg | Vit. C/ PL × 100 | OSI 110° C., h | PF | Stability at 15° C. after 30d |
|---|---|---|---|---|---|---|---|
| 16a | — | — | — | — | 5 | 1 | Clear |
| 16 | 2500 | 250 | 200 | 10 | 12.3 | 2.4 | Clear |
| 17 | 5000 | 500 | 200 | 10 | 16 | 3.2 | Clear |
| 18 | 7500 | 750 | 200 | 10 | 18 | 3.6 | Clear |
| 19 | 10000 | 1000 | 200 | 10 | 20 | 4 | Clear |

Examples 20–24

Following the procedure of Example 1 to stabilize blackcurrant seed oil (BCSO), BCSO stabilized with a constant ratio of vit.C to PL is evaluated for stability in storage, OSI and PF. The results are set out in Table 5 below by comparison with the unprotected oil (20a) and with the same oil to which 1.66% of a ternary mixture of vit.C, PL and vit.E in quantities of 1000 mg/kg vit.C, 4500 mg/kg PL and 500 mg/kg vit.E (20b) has been added.

TABLE 5

| Example | PL mg/kg | Vit. C mg/kg | EDTA mg/kg | Vit. E mg/kg | Vit. C/ PL × 100 | OSI 100° C., h | PF | Stability at 15° C. after 20d |
|---|---|---|---|---|---|---|---|---|
| 20a | — | — | — | — | — | 4 | 1 | Clear |
| 20b | 4500 | 1000 | — | 500 | 22 | 17.5 | 4.38 | Slightly cloudy |
| 20 | 10000 | 1000 | — | — | 10 | 19.8 | 4.95 | Clear |
| 21 | 10000 | 1000 | — | 500 | 10 | 17.6 | 4.4 | Clear |
| 22 | 10000 | 1000 | 400 | — | 10 | 24 | 6 | Clear |
| 23 | 10000 | 1000 | 400 | 500 | 10 | 20.2 | 5.05 | Clear |
| 24 | 5000 | 500 | 200 | — | 10 | 17.2 | 4.3 | Clear |

The results confirm those obtained with SFO (Examples 11 to 15), namely that the addition of vit.E does not improve the stability of BCSO to oxidation but would actually seem to have a pro-oxidizing effect in a vegetable oil naturally containing around 750 ppm of vit.E (Example 22 compared with 23).

Example 25

Following the procedure of Example 1 to stabilize chicken fat free from vit.E, the chicken fat is evaluated for OSI, PF and colour with and without added vit.E by comparison with the unprotected fat. The results obtained are set out in Table 6 below.

TABLE 6

| PL mg/kg | Vit. C mg/kg | Vit. E mg/kg | EDTA mg/kg | OSI 120° C., h | PF | Color after Rancimat |
|---|---|---|---|---|---|---|
| — | — | — | — | 2 | 1 | Yellow |
| 5000 | 500 | — | — | 7.3 | 3.65 | Yellow |
| 5000 | 500 | 250 | — | 16.5 | 8.25 | Orange |
| 5000 | 500 | — | 100 | 10.5 | 5.25 | Yellow |
| 5000 | 500 | 250 | 100 | 19.3 | 9.65 | Yellow |

The above results confirm that the synergistic effect between vit.C and vit.E exists when the fat to be protected does not naturally contain vit.E.

Example 26

A soya lecithin free from PC (other PLS fraction), which has been obtained as second fraction by liquid chromatography in a column of silica gel using a mixture of hexane, 2-propanol and water in a ratio of 1:1:0.1, is dissolved in SFO. A first fraction rich in phosphatidyl choline (PC fraction) is also collected.

Quantities of 10,000 mg/kg of each phospholipid fraction, 1000 mg/kg of vit.C and 200 mg/kg of EDTA in solid form and then 5% of demineralized water are added to the oil. After vigorous stirring under nitrogen for 15 minutes at 20° C., a heterogeneous mixture is obtained and is dried for 30 minutes at 80 to 90° C. under a pressure of 35 mbar and then 0.5 mbar. Filtration gives a homogeneous micellar phase in the case of the oil stabilized with the other PLS fraction. By contrast, the PC fraction could not be dissolved in oil.

The OSI is then evaluated. The results are set out in Table 7 below.

TABLE 7

| Phospholipids | OSI 110° C. | Remarks |
|---|---|---|
| PC Fraction | — | The fraction could not be dissolved in the oil |
| Other PLS fraction | 21 | The fraction dissolves in the oil which is perfectly clear |

Examples 27–31

SFO is stabilized with various water-soluble antioxidant active principles in the same way as described in Example 26. The results are set out in Table 8 below. SFO with no additive (27a) was evaluated for comparison.

The phenyl indanes were obtained from coffee by the extraction process according to European Patent Application No. 94109355.1 filed on 17.06.1994 under the title "Phenyl indanes, a process for their production and their uses".

TABLE 8

| Example | PL mg/kg | Active principle (AP) | AP mg/kg | EDTA mg/kg | OSI 110° C., h | PF |
|---|---|---|---|---|---|---|
| 27a | — | — | — | — | 5 | 1 |
| 27 | 10000 | L-histidine | 1000 | 200 | 11.5 | 2.3 |
| 28 | 10000 | L-cysteine | 1000 | 200 | 12 | 2.4 |
| 29 | 10000 | Rosemary extract | 1000 | 200 | 14 | 28 |
| 30 | 10000 | Green tea extract | 1000 | 200 | 12 | 2.4 |
| 31 | 10000 | phenyl indanes | 500 | — | 30.5 | 6.1 |

Examples 32–33

The procedure described in Example 1 up to hydration of the PLS is used to stabilize an SFO. The drying step is carried out at various temperatures. The antioxidant properties and the color of the stabilized oils are evaluated by comparison with the unstabilized oil (32a). The results are set out in Table 9 below.

TABLE 9

| Example | Drying temperature | PL without PC | Vit. C mg/kg | EDTA mg/kg | OSI 110° C., h | PF | Color measurement Lovibond 5.25" Y | R |
|---|---|---|---|---|---|---|---|---|
| 32a | — | — | — | — | 5 | 1 | 8.4 | 1.3 |
| 32 | 80–90° C. | 10000 | 1000 | 400 | 21 | 4.2 | 43 | 4.8 |
| 33 | 60–70° C. | 10000 | 1000 | 400 | 22.8 | 4.56 | 18.5 | 2.7 |

What is claimed is:

1. A process for incorporating a water-soluble active principle in a fat which comprises treating phospholipids to produce a phospholipid fraction which is substantially free from phosphatidyl choline, forming a mixture of the phospholipid fraction and liquid fat, adding a water soluble active principle to a quantity of water with agitation for a sufficient period of time of about 10 to 30 minutes at a temperature of about 60° C. to about 80° C. and under an atmosphere sufficient to incorporate the water-soluble active principle into the water, adding a sufficient amount of the water to hydrate the phospholipid fraction to hydrate it and form a heterogeneous mixture, and drying the heterogeneous mixture to form a homogeneous composition.

2. A process as claimed in claim 1, wherein the treating step comprises mixing the phospholipids with the liquid fat to form an oil solution, treating the oil solution with an adsorbent to remove phosphatidyl choline from the phospholipids and separating the adsorbent from the oil solution.

3. A process as claimed in claim 1, wherein the treating step comprises mixing the phospholipids with one or more solvents to form a solvent solution, treating the solvent solution to liquid chromatography to separate the phospholipid fraction from the phosphatidyl choline and most of the triglycerides.

4. A process as claimed in claim 1, which further comprises selecting the water-soluble active principles to be cosmetic agents, dermatological agents, antioxidants, or sequestering agents.

5. A process as claimed in claim 1, which further comprises selecting the liquid fat to be rich in unsaturated fatty acids.

6. The method of claim 1 wherein the water-soluble active principle is incorporated into the water with vigorous stirring in the absence of air at a temperature of above about 60° C. to about 80° C. for at least about 10 to about 30 minutes.

7. A process as claimed in claim 1, which further comprises adding the water soluble active principle to the water in dried form.

8. A process as claimed in claim 7, wherein the amount of water represents about 2 to 8% by weight of the mixture and hydration takes place for about 10 to 30 minutes in the absence of air which results in the formation of the heterogeneous mixture.

9. A process as claimed in claim 7, which further comprises removing the water from the heterogeneous mixture by heating the mixture to about 60–90° C. under a vacuum of about 0.5 to 35 mbar to obtain a homogeneous composition as a micellar phase.

10. A food, cosmetic or pharmaceutical product containing a homogeneous composition of a water-soluble active principle in a fat, said composition prepared by the process of claim 1.

11. A process as claimed in claim 2, which further comprises treating the oil solution with an adsorbent comprising a bleaching earth in an amount which is greater than the amount of phospholipids to thus remove substantially all of the phosphatidyl choline from the phospholipids and form the phospholipid fraction.

12. A process as claimed in claim 11 wherein the bleaching earth is added an amount of at least about four times greater than the amount of phospholipids to remove substantially all of the phosphatidyl choline from the phospholipids and form the phospholipid fraction.

13. A process as claimed in claim 4, which further comprises selecting the water-soluble active principles to be vitamin C, vegetable extracts, organic acids, or amino acids.

14. A process as claimed in claim 5, which further comprises selecting the liquid fat to be sunflower oil, wheat germ oil, grapeseed oil, corn oil, safflower oil, olive oil, evening primrose oil, borage oil, blackcurrent seed oil, chicken fat, butter oil or a marine animal oil.

15. A process as claimed in claim 1, which further comprises providing the homogeneous composition with an oil stability index of at least about 11.5 hours at 110° C.

16. A process as claimed in claim 1, wherein the water-soluble active ingredient is vitamin C and the weight ratio of vitamin C to the phospholipid fraction is less than or equal to about 13% to ensure optimal stability of the composition.

17. The method of claim 6 wherein the water-soluble active principle is incorporated into the water under a nitrogen atmosphere at a temperature of about 80° C. for about 10 to 30 minutes.

* * * * *